United States Patent
Wang et al.

(10) Patent No.: US 10,139,325 B2
(45) Date of Patent: Nov. 27, 2018

(54) SYSTEM AND METHOD FOR EVALUATING BUBBLE FORMATION POTENTIAL IN A STRUCTURE

(71) Applicant: THE BOEING COMPANY, Chicago, IL (US)

(72) Inventors: Xiaoxi Wang, Mukilteo, WA (US); Jeffrey C. Mentel, Stanwood, WA (US); Shuying Zhu, Renton, WA (US); Stephen P. Jones, Snoqualmie, WA (US)

(73) Assignee: The Boeing Company, Chicago, IL (US)

(*) Notice: Subject to any disclaimer, the term of this patent is extended or adjusted under 35 U.S.C. 154(b) by 193 days.

(21) Appl. No.: 15/218,451

(22) Filed: Jul. 25, 2016

(65) Prior Publication Data
US 2017/0307493 A1    Oct. 26, 2017

Related U.S. Application Data

(60) Provisional application No. 62/325,567, filed on Apr. 21, 2016.

(51) Int. Cl.
*G01N 17/00* (2006.01)
*G01N 21/17* (2006.01)
*G01N 3/12* (2006.01)

(52) U.S. Cl.
CPC .............. *G01N 3/12* (2013.01); *G01N 17/002* (2013.01); *G01N 21/17* (2013.01)

(58) Field of Classification Search
CPC ............. G01N 3/12; G01N 3/56; G01N 17/00; G01N 17/002; G01N 17/04; G01N 21/01;
(Continued)

(56) References Cited

U.S. PATENT DOCUMENTS

| 4,794,804 A | * | 1/1989 | Ishii | G01N 17/00 73/865.6 |
| 5,034,190 A | * | 7/1991 | Economy | G01N 17/00 422/111 |

(Continued)

FOREIGN PATENT DOCUMENTS

| CN | 202502035 U | * | 10/2012 | ............ G01N 17/00 |
| CN | 203350162 U | * | 12/2013 | ............ G01N 17/00 |

(Continued)

OTHER PUBLICATIONS

European Patent Office; Office Action for European Patent Application No. 17158610.0 dated Aug. 7, 2017, 8 Pages.

*Primary Examiner* — Nguyen Ha
(74) *Attorney, Agent, or Firm* — Charles L. Moore; Moore & Van Allen PLLC (57) ABSTRACT

A system for evaluating bubble formation potential in a structure includes an environment test chamber and an environmental controller for controlling a plurality of environmental conditions within the environment chamber. The system additionally includes a detector for capturing images of a structure under test and an illumination source for controlling illumination of the structure under test. A user interface is coupled to the environment controller for setting and adjusting environmental conditions within the environment test chamber. The user interface is also coupled to the illumination source for setting and adjusting illumination of the structure and the user interface is coupled to the detector for receiving the captured images and evaluating bubble formation potential in the structure under test based on the captured images.

20 Claims, 6 Drawing Sheets

(58) Field of Classification Search
CPC ........ G01N 21/17; G01N 25/00; G01N 25/72; G01N 29/00; G01N 29/22; G01D 18/00
See application file for complete search history.

(56) References Cited

U.S. PATENT DOCUMENTS

| | | |
|---|---|---|
| 5,854,433 A | 12/1998 | Patel et al. |
| 6,023,985 A | 2/2000 | Fournier |
| 9,404,840 B2 * | 8/2016 | Hondroulis ............ G01N 3/30 |
| 2002/0139928 A1 | 10/2002 | Rathod et al. |
| 2013/0125676 A1 | 5/2013 | Tockstein et al. |
| 2013/0193219 A1 | 8/2013 | Xia et al. |
| 2014/0240694 A1 * | 8/2014 | Scheumann ........... G01N 21/90 356/36 |
| 2015/0355074 A1 | 12/2015 | Zhou et al. |
| 2016/0363525 A1 * | 12/2016 | Friedersdorf ............ G01N 3/02 |

FOREIGN PATENT DOCUMENTS

| | | | | |
|---|---|---|---|---|
| CN | 204666567 U | * | 9/2015 | ............. G01N 29/22 |
| CN | 104964912 A | * | 10/2015 | ............. G01N 17/00 |
| JP | 2012058151 A | * | 3/2012 | ............. G01N 17/00 |

\* cited by examiner

SYSTEM AND METHOD FOR EVALUATING BUBBLE FORMATION POTENTIAL IN A STRUCTURE

CROSS-REFERENCE TO RELATED APPLICATIONS

This application claims the benefit of U.S. Provisional Application No. 62/325,567, filed Apr. 21, 2016.

FIELD

The present disclosure relates to testing and evaluating structures, and more particularly to a system and method for evaluation bubble formation potential in a structure.

BACKGROUND

The formation of bubbles in structures, such as laminated structures that may include a decorative layer of material attached to a surface of another layer material is a recurring problem in numerous industries including, for example, construction, aviation, automobile, marine, train, recreation and printing industries. Depending on individual applications, bubble formation is often unpredictable and difficult to eliminate. The appearance of bubbles in decorative surfaces of such structures may occur only after a considerable length of time, e.g., days or even months and as a result of certain environmental conditions. When bubble formation occurs, the decorative laminate must be removed and the underlying surface is cleaned. The decorative laminate is then reapplied. This process is typically a time and labor intensive procedure without any assurances the bubbling will not reoccur. Accordingly, there is a need to predict or evaluate a potential for the formation of bubbles in different structures, evaluate bubbling mitigation measures and enable development of bubble-free structures.

SUMMARY

In accordance with an example, a system for evaluating bubble formation potential in a structure includes an environment test chamber and an environmental controller for controlling a plurality of environmental conditions within the environment chamber. The system additionally includes a detector for capturing images of a structure under test and an illumination source for controlling illumination of the structure under test. A user interface is coupled to the environment controller for setting and adjusting environmental conditions within the environment test chamber. The user interface is also coupled to the illumination source for setting and adjusting illumination of the structure and the user interface is coupled to the detector for receiving the captured images and evaluating bubble formation potential in the structure under test based on the captured images.

In accordance with another example, a system for evaluating bubble formation potential in a structure includes an environment test chamber; a temperature controller for controlling a temperature within the environment test chamber; a humidity controller for controlling humidity within the environment test chamber; and a pressure controller for controlling air pressure or vacuum within the environment test chamber. The system also includes a detector for capturing images of a structure under test and an illumination source for controlling illumination of the structure under test. The system additionally includes a user interface coupled to the temperature controller, the humidity controller and the pressure controller for setting and adjusting environmental conditions within the environment test chamber. The user interface is also coupled to the illumination source for setting and adjusting illumination of the structure under test. The user interface is also coupled to the detector for receiving the captured images of the structure under test.

In accordance with a further example, a method for evaluating bubble formation potential in a structure includes setting a plurality of environmental conditions within the environment test chamber containing the structure. The method also includes capturing images of the structure over a predetermined time interval. The method additionally includes detecting bubble formation in the structure and evaluating the bubble formation in response to detecting the bubble formation in the structure.

In accordance with another example or any of the previous examples, the detector and illumination source are contained in the environment test chamber.

In accordance with another example or any of the previous examples, the detector is outside the environment test chamber.

In accordance with another example or any of the previous examples, the environment test chamber is a portable environment test chamber.

In accordance with another example or any of the previous examples, the user interface is at remote geographic location from the environment test chamber.

In accordance with another example or any of the previous examples, the system includes a sample holder for holding the structure under test and the sample holder includes a mechanism for positioning the structure under test at different angles relative to the detector.

In accordance with another example or any of the previous examples, the user interface includes a computer system and an algorithm running on the computer system that is configured to evaluate the images from the detector to determine a bubble formation potential of the structure under test based on environmental conditions within the environment test chamber.

In accordance with another example or any of the previous examples, the system may also include at least one of a radiation level sensor for detecting a radiation level within the environment test chamber; a particle level sensor to detect a level of particles within the environment test chamber; a bacteria sensor to detect any bacteria within the environment test chamber; and an illumination sensor to detect an amount of illumination of the structure under test.

In accordance with another example and any of the previous examples, the system may also include at least one other environment controller for controlling at least one of a radiation level within the environment test chamber, a particle level within the environment test chamber and bacteria within the environment test chamber.

In accordance with another example and any of the previous examples, the system may include a sample holder for holding a plurality of structures for evaluating bubble formation potential simultaneously and a plurality of detectors for capturing images of at least a front side and a back side of each structure.

In accordance with another example and any of the previous examples, the sample holder may be configured for moving the structures relative to the detectors.

In accordance with another example and any of the previous examples, the system may further include a positioning mechanism associated with the detectors for moving the detectors relative to the structures.

DETAILED DESCRIPTION

The following detailed description of examples refers to the accompanying drawings, which illustrate specific examples of the disclosure. Other examples having different structures and operations do not depart from the scope of the present disclosure. Like reference numerals may refer to the same element or component in the different drawings. Although the disclosure is intended for space-based thrusters, the disclosure does not limit the use to spacecraft.

Certain terminology is used herein for convenience only and is not to be taken as a limitation on the examples described. For example, words such as "proximal", "distal", "top", "bottom", "upper," "lower," "left," "right," "horizontal," "vertical," "upward," and "downward", etc., merely describe the configuration shown in the figures or relative positions used with reference to the orientation of the figures being described. Because components of examples can be positioned in a number of different orientations, the directional terminology is used for purposes of illustration and is in no way limiting. Based on the disclosure herein, it is to be understood that other examples may be utilized and structural or logical changes may be made without departing from the scope of the present disclosure. The following detailed description, therefore, is not to be taken in a limiting sense, and the scope of the present disclosure is defined by the appended claims.

In accordance with an example, a portable testing apparatus or system and method is provided for evaluating bubble formation potential in a laminated structure or test sample. The system and method is configured to simulate a variety of environmental conditions to induce bubble formation in a surface of the laminated structure or test sample. Data is collected about inducing the bubble formation for analysis or evaluation. The data collected includes capturing images of the laminated structure or test sample under the variety of environmental conditions. The captured images are evaluated to detect bubble formation under the variety of environmental conditions. The bubble formation detected is evaluated to determine the bubble formation potential of the laminated structure under test under normal or real-life application or use of the structure.

Figure 1:
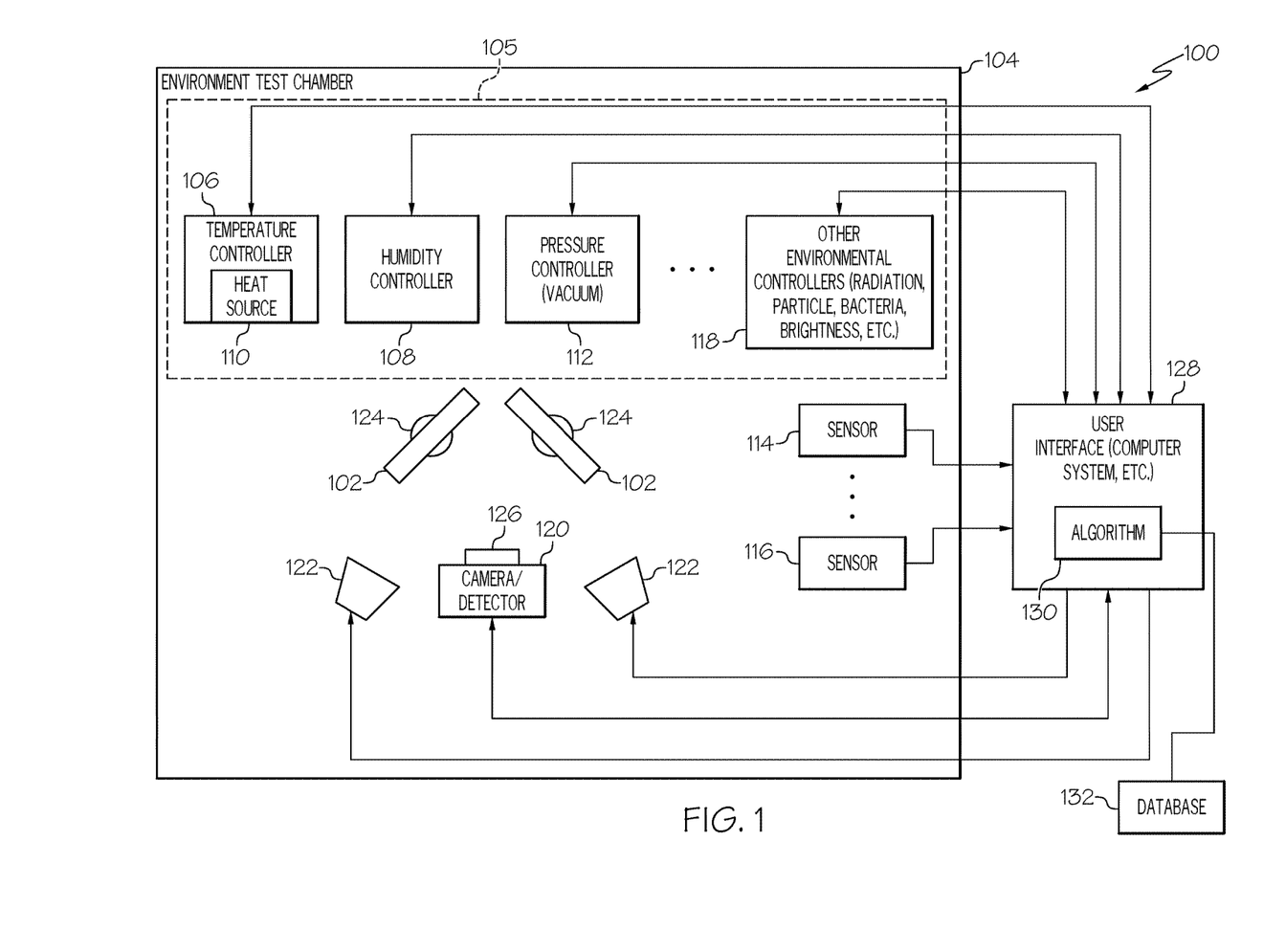
FIG. 1 is a block schematic diagram of an example of a system for evaluating bubble formation potential in a structure in accordance with an example of the present disclosure.

FIG. 1 is a block schematic diagram of an example of a system 100 for evaluating bubble formation potential in a structure 102 or test sample in accordance with an example of the present disclosure. The system 100 includes an environment test chamber 104. Depending on the size of the environment test chamber 104, more than one structure 102 or test sample may be evaluated at a time. The structure 102 or test sample is a laminated structure. The laminated structure may include an upper or outer layer of material that is disposed on a lower or underlying layer of another material. The upper or outer layer of material may be a layer of decorative material. The outer layer of material may be attached or adhered to a surface of the underlying layer of other material by an adhesive, bonding agent or other mechanism for fixedly securing the outer layer of material to the underlying layer of material. The outer layer of material may be much thinner and pliable compared to the underlying layer of material. The underlying layer of material may be a rigid, stronger material to provide structural support. For example, the structure 102 or laminated structure may be a panel or other component used in an interior of an aircraft or other vehicle.

The system 100 also includes one or more environment controllers 105 for controlling a plurality of environmental conditions within the environment test chamber 104. The one or more environment controllers 105 include, but are not necessarily limited to, a temperature controller 106 for controlling a temperature within the environment test chamber 104; a humidity controller 108 for controlling humidity within the environment test chamber 104; and a pressure controller 112 for controlling an air pressure or vacuum within the environment test chamber 104. The one or more environment controllers 105 may independently control the environmental conditions within the environment test chamber 104. In accordance with an example, the temperature controller 106 includes a heat source 110. The temperature controller 106, humidity controller 108 and pressure controller 112 are within the environment test chamber 104 as shown in the example in FIG. 1. In another example, the temperature controller 106, humidity controller 108 and pressure controller 112 are outside of the environment test chamber 104 and elements for modifying or adjusting the temperature, humidity and pressure within the environment test chamber 104 reside within the environment test chamber 104 or are associated with the environment test chamber 104.

A plurality of sensors 114-116 within the environment test chamber 104 detect or sense the environmental conditions within the environment test chamber 104. The plurality of sensors 114-116 includes but is not necessarily limited to a temperature sensor, a humidity sensor and a pressure sensor. The temperature sensor, humidity sensor and pressure sensor are respectively associated with the temperature controller 106, humidity controller 108 and pressure controller 112 for controlling environmental conditions within the environment test chamber 104.

In accordance with other examples, the system 100 also includes one or more other types of environment controllers 118. For example, the system 100 includes controllers for controlling at least one of a radiation level within the environment test chamber 104, a particle level within the environment test chamber 104, a bacteria level within the environment test chamber 104, and a brightness or illumination level on the structure 102 or structures under test.

The plurality of sensors 114-116 may also include a radiation level sensor, a particle level sensor, a bacteria sensor or bacterial level sensor, and a light sensor to detect an amount of illumination of the structure 102 or structures 102 under test.

The system 100 additionally includes one or more detectors 120 or cameras for capturing images of the structure 102 under test and one or more illumination sources 122 or light sources for controlling illumination of the one or more structures 102 under test. In accordance with an example, the one or more detectors 120 are digital single lens reflex (DSLR) cameras with a time elapsing function that can take a picture at preset time intervals, such as for example about every 5 minutes. In another example, the one or more detectors 120 are video cameras that have a frame speed that permits images to be extracted at a predetermined frequency. The operating parameters of the one or detectors 120 are set to achieve clear close-up images so that bubble formation is accurately captured or captured with sufficient resolution to detect the bubbles.

The one or more illumination sources 122 include an adjustable wavelength feature that permits emitting light in all visible colors. An optimal wavelength of the illumination source 122 is dependent on a color of a substrate or surface of the structure 102 under test for best visibility in capturing images of the bubble formation. In accordance with an example, the one or more illumination sources 122 are between about 1 inch and about 10 feet from the structure 102 under test. The illumination sources 122 are controllable to provide an illumination level and contrast of the structure 102 under test that the detector 120 or detectors can capture images for detecting bubbles with a dimension or diameter as small as about 1/32 inch or larger at certain illumination and contrast settings.

In accordance with other examples, the one or more detectors 120 and illumination sources 122 include devices or detection systems that emit and detect invisible light or light energy in other spectrums including but not necessarily limited to Gamma rays, X-rays, ultraviolet, infrared, microwave or other forms of radiation or illumination. In other examples, laser emission and detection devices or systems are used. Semiconductor strain gauges, such as piezoresistors or the like, may also be utilized to detect bubble formation.

In accordance with an example, a sample holder 124 is provided for holding each structure 102 under test. In other examples, a single sample holder holds multiple structures 102 under test. The sample holder 124 includes a mechanism for positioning the structure 102 under test at different angles relative to a lens 126 or receiver of the detector 120. The mechanism moves or pivots a surface of the structure 102 under test between an angle of about zero degrees and about 90 degrees relative to the lens 126 or receiver of the detector 120. Examples of sample holders 124 include but are not necessarily limited to clamp-on devices, vacuum devices or electromagnetic devices. In another example, multiple detectors 120 are used to view the structure 102 or structures 102 under test at different angles between about zero degrees and about 90 degrees relative to a plane of a surface of the structure 102.

The system 100 further includes a user interface 128 coupled to the environment test chamber 104. The user interface 128 may be a remote user interface similar to that described with reference to FIG. 3. The user interface 128 is coupled to the temperature controller 106, the humidity controller 108 and the pressure controller 112 for setting and adjusting environmental conditions within the environment test chamber 104. The user interface 128 is also coupled to the one or more illumination sources 122 for setting and adjusting illumination of the structure 102 or structures under test. The user interface 128 is configured for controlling the controllers 106, 108, 112 and 118 either together or independently for modifying the environmental conditions within the environment chamber 104. The user interface 128 is also configured for controlling the illumination of the structure 102 or structures by the one or more illumination sources 122 together with the controllers or independently. The user interface 128 is also coupled to the detector 120 or detectors for receiving the captured images of the structure 102 or structures under test for detecting bubbles.

In accordance with an example, the user interface 128 includes a computer system or other electronic device for performing evaluation of the structure 102 or structures under test based on images captured by the detector 120 or detectors. The system 100 further includes an algorithm 130 or module running on the computer system. The algorithm 130 is configured to determine bubble formation potential of the structure 102 or structures under test based on environmental conditions within the environment test chamber 104. The algorithm 130 evaluates the images from the detector 120 or detectors and detects bubble formation from evaluation of the images. In accordance with an example, the algorithm 130 uses a database 132 for evaluating the bubble formation potential of the structure 102. The database 132 contains performance relationships of different structures between extreme environmental conditions within the environment test chamber 104 and normal environmental conditions or real-life environmental conditions under which the structures may be exposed during their useful life and/or normal intended use. The database 132 contains performance relationships for multiple different structures that may be tested in the environment test chamber 104. The extreme environmental conditions used for testing structures 102 within the environment test chamber 104 is intended to accelerate the process of bubble formation or ageing of the structure 102 compared to the environmental conditions the structure 102 would be exposed to under normal or real-life application or use of the structure 102. Bubble formation potential in the structure 102 under normal or real-life environmental conditions is determinable from the performance relationships in the database 132 by the algorithm 130 in a much shorter period of time by applying the extreme environmental conditions in the environment test chamber 104 to cause bubble formation.

Figure 2:
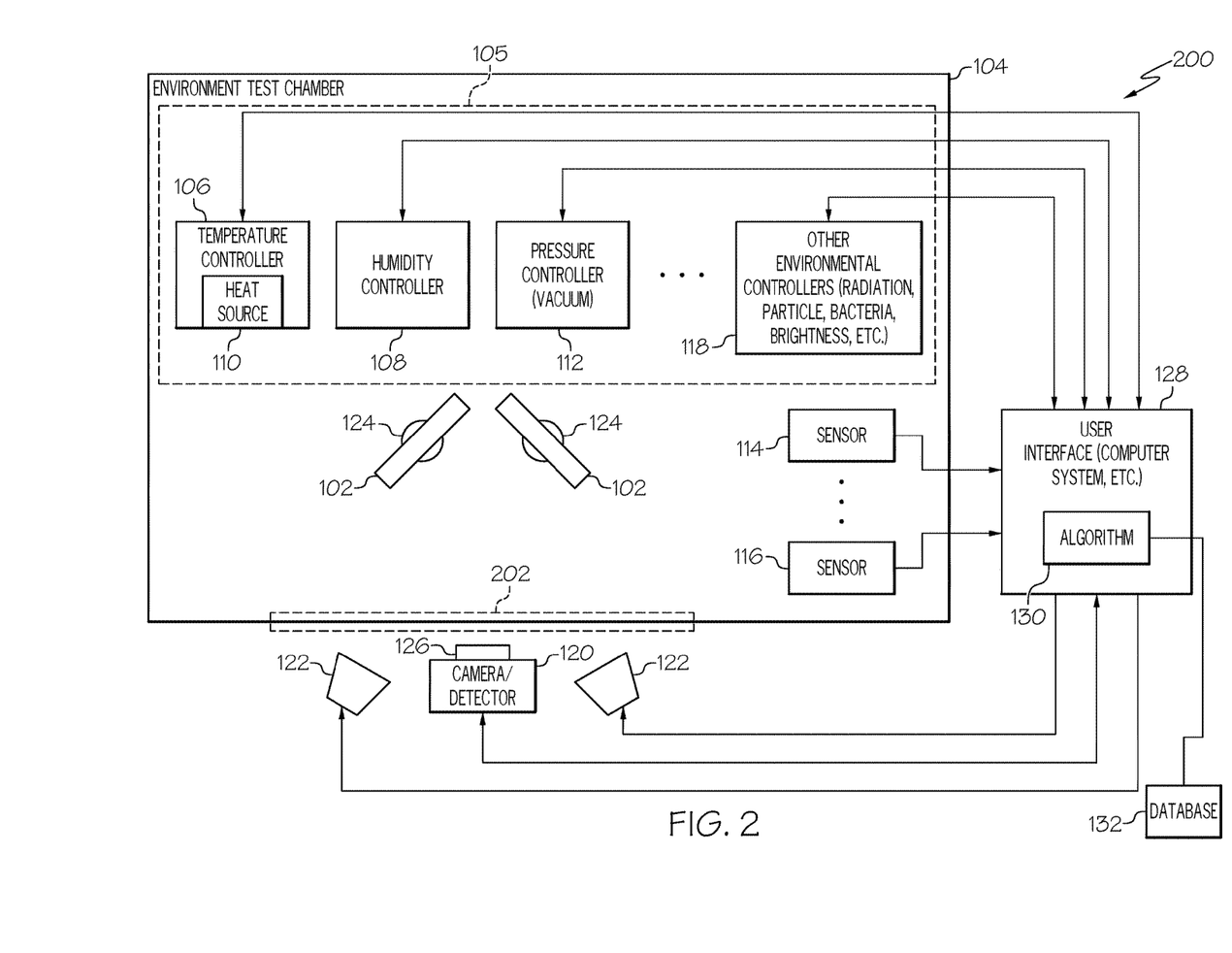
FIG. 2 is a block schematic diagram of an example of a system for evaluating bubble formation potential in a structure in accordance with another example of the present disclosure.

Referring to FIG. 2, FIG. 2 is a block schematic diagram of an example of a system 200 for evaluating bubble formation potential in a structure in accordance with another example of the present disclosure. In the example illustrated in FIG. 1, the detector 120 and illumination sources 122 are contained within the environment test chamber 104. In the example illustrated in FIG. 2, the detector 120 of the system 200 is outside the environment test chamber 104. The illumination sources 122 are also outside the environment test chamber 104 as shown in the example in FIG. 2. In another example, the illumination sources 122 are inside the environment test chamber 104 similar to that shown in FIG. 1 and the detector 120 is outside the environment test chamber 104. If the detector 120 is outside the environment test chamber 104, the environment test chamber 104 includes a viewing window 202 through which the detector 120 can capture images of the structure 102 under test while an evaluation for bubble formation potential is being performed.

Figure 3:
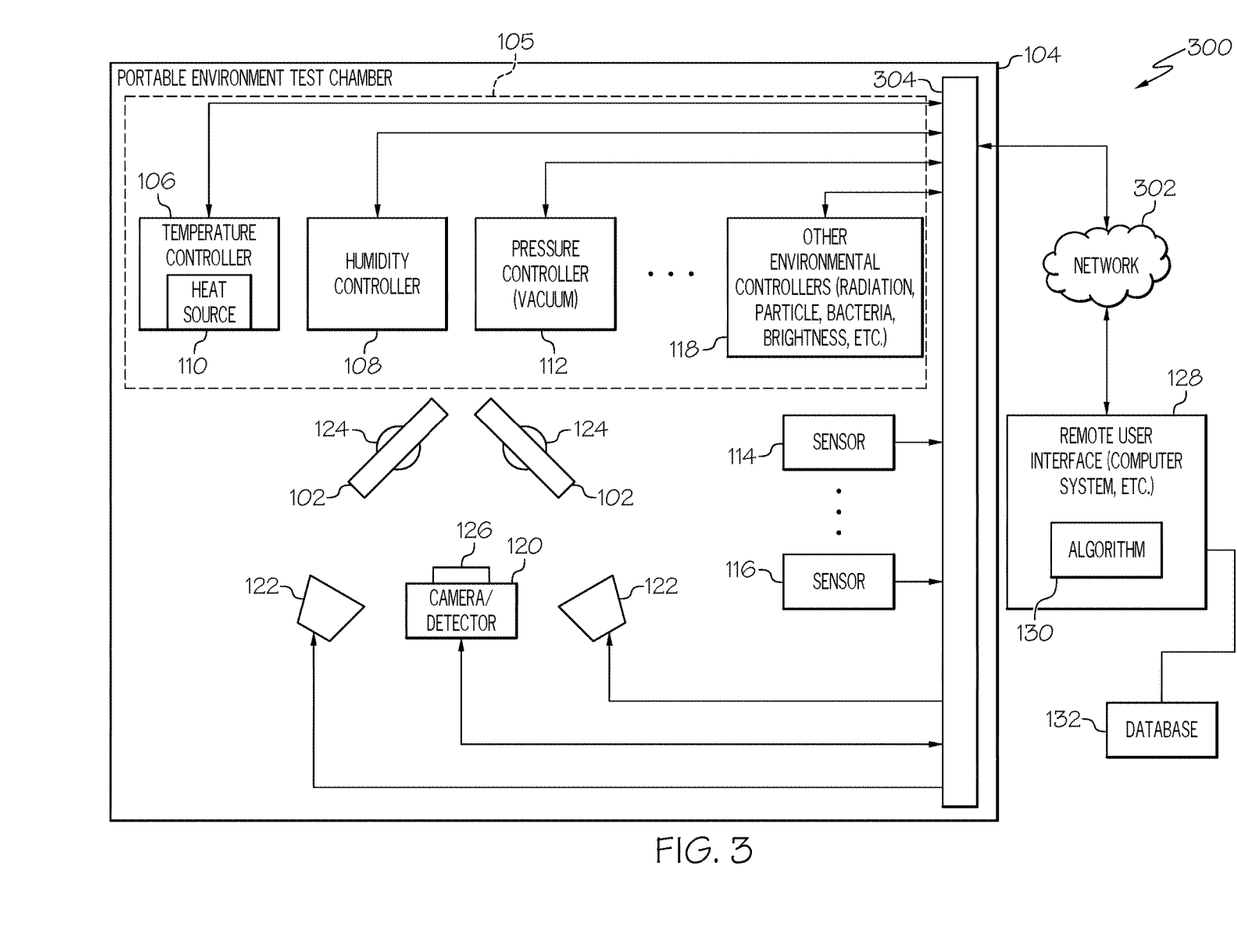
FIG. 3 is a block schematic diagram of an example of a system for evaluating bubble formation potential in a structure in accordance with a further example of the present disclosure.

Referring to FIG. 3, FIG. 3 is a block schematic diagram of an example of a system 300 for evaluating bubble formation potential in a structure in accordance with a further example of the present disclosure. The user interface 128 is a remote user interface, that is, the remote user interface 128 is at a remote geographic location from the environment test chamber 104. In accordance with an example, the environment test chamber 104 is a portable environment test chamber. The portable environment test chamber 104 is transported by an owner of the system 100 to a manufacturer or supplier of the structures 102 for testing and evaluation of different laminated structure constructs. The remote user interface 128 is at the owner's location or place of business which is at a different geographic location from the manufacturer's or supplier's place of business. The remote user interface 128 is coupled via a network 302 or other communications link to the environment test chamber 104. The network 302 may be the Internet, a proprietary network or other type network that may be a secure network. The controllers 106, 108, 112 and 118, detector 120 and illumination sources 122 are controlled by the remote user interface 128 via the network 302. Images captured by the detector 120 are transmitted back to the remote user interface 128 via the network 302, either together or independently. In accordance with an example, the system 300 includes a network interface 304 associated with the environment test chamber 104 through which the controllers 106, 108, 112 and 118, detector 120 and illumination sources 122 are coupled to the network 302 and by the network 302 to the remote user interface 128.

Figure 4:
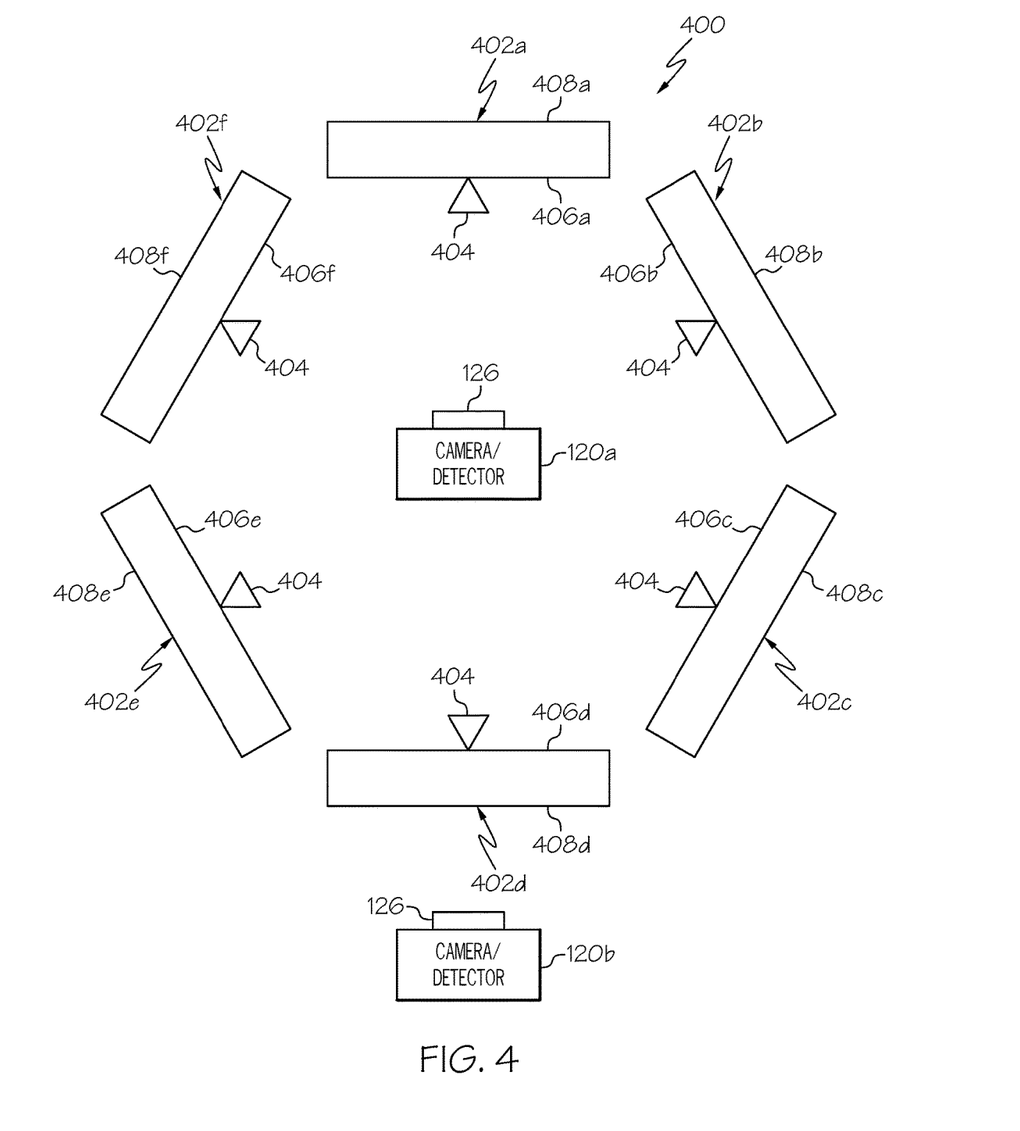
FIG. 4 is a block schematic diagram of an example of an arrangement for evaluating multiple structures or test samples simultaneously in accordance with another example of the present disclosure.

FIG. 4 is a block schematic diagram of an example of an arrangement 400 for evaluating multiple structures 402a-402f or test samples simultaneously in accordance with another example of the present disclosure. The arrangement 400 may be used in association with any of the systems 100, 200 or 300 described with reference to FIGS. 1-3. The arrangement 400 includes a single sample holder or a plurality of sample holders 404 configured for holding the multiple structures 402a-402f The arrangement also includes one or more detectors 120a and 120b or cameras. In the example illustrated in FIG. 4, the arrangement 400 includes at least two detectors 120a and 120b.

The multiple structures 402a-402f are arranged by the sample holders 404 around at least a first detector 120a for capturing images of a first surface 406a-406f or front side of each structure 402a-402f for evaluating bubble formation potential in the structures 402a-402f. Accordingly, the first detector 120a is positioned in a center of the structures 402a-402f which defines a circle or other geometric shape surrounding the first detector 120a. At least a second detector 120b is positioned outside the structures 402a-402f or on an opposite side of the structures 402a-402f from the first detector 120a. The second detector 120b is positioned for capturing images of a second surface 408a-408f or back side of each structure 402a-402f for evaluating bubble formation potential in the structures 402a-402f.

In accordance with other examples, the arrangement 400 includes only the first detector 120a or a plurality of detectors 120a with the multiple structures 402a-402f surrounding the detector 120a or detectors 120a, or the arrangement 400 includes only the second detector 120b or a plurality of detectors 120b positioned outside the structures 402a-402f.

In accordance with an example, the sample holder or sample holders 404 are configured for movement relative to four-axes for positioning the structures 402a-402f relative to the first detector 120a and the second detector 120b for capturing images of the surfaces of the structures 402a-402f during evaluation of bubble formation potential as described herein. For example, the sample holder or sample holders 404 rotate the structures 402a-402f about the first detector 120a and move each structure 402a-402f in X, Y, and Z axes directions relative to a lens 126 or radiation receiver of each detector 120a and 120b. The first detector 120a and the second detector 120b may remain stationary or fixed in location. In accordance with an example, the structures 402a-402f are moved simultaneously so that each structure 402a-402f is moved in front of the detectors 120a and 120b for capturing the images of the surfaces of the structures 402a-402f In another example, the structures 402a-402b are moved by the sample holder or holders 404 intermittently and the images are captured when the structures 402a-402b are stationary. In a further example, the structures 402a-402b are moved by the sample holder or holders 404 continuously. The detector settings are adjusted to capture clear images of the moving structures 402a-402b.

Figure 5:
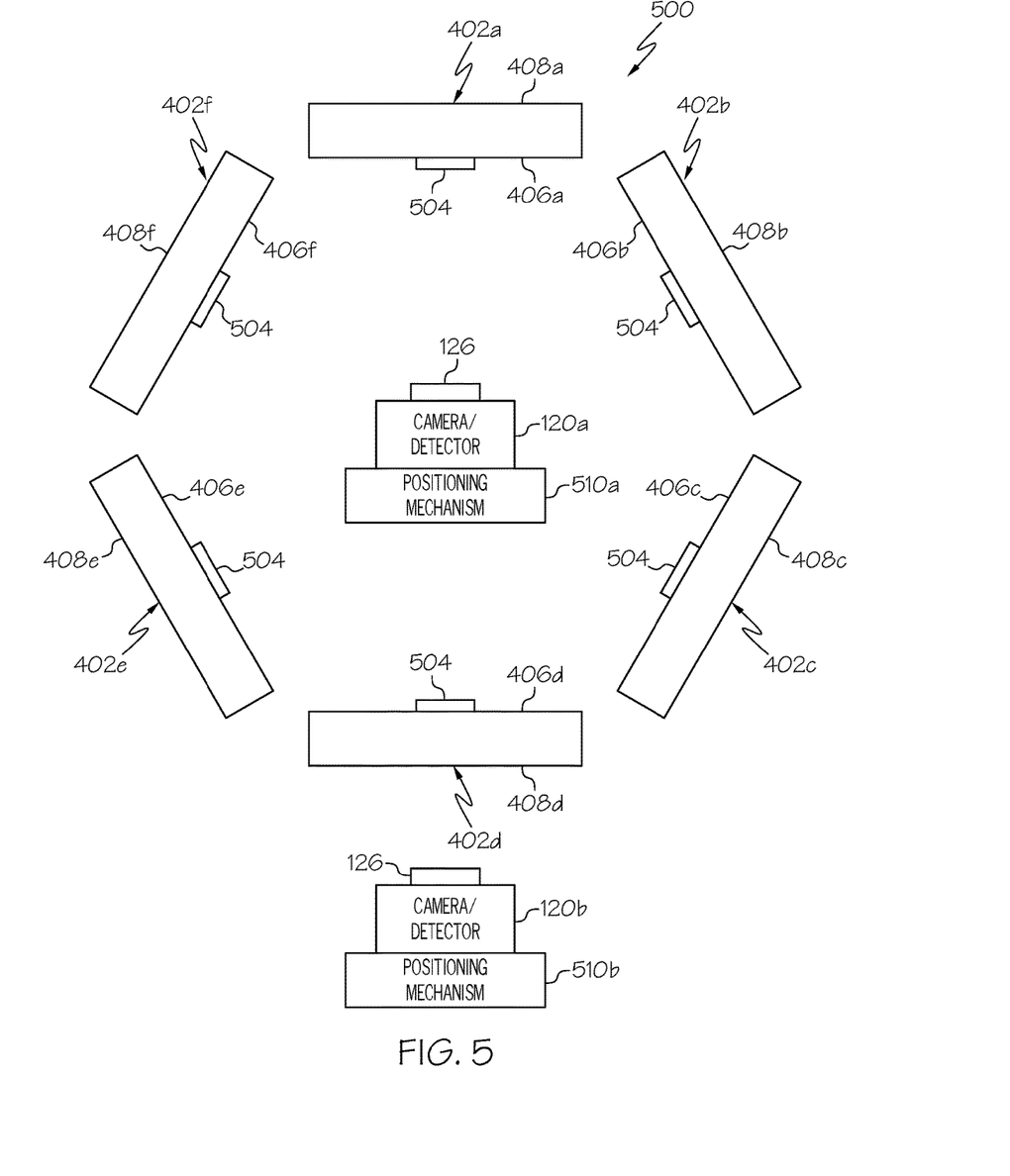
FIG. 5 is a block schematic diagram of an example of an arrangement for evaluating multiple structures or test samples simultaneously in accordance with a further example of the present disclosure.

FIG. 5 is a block schematic diagram of an example of an arrangement 500 for evaluating multiple structures 402a-402f or test samples simultaneously in accordance with a further example of the present disclosure. The arrangement 500 may be used in association with any of the systems 100, 200 or 300 described with reference to FIGS. 1-3. The arrangement 500 may be similar to the arrangement 400 in FIG. 4 except a single sample holder or a plurality of sample holders 504 remain stationary or fixed in location and the detectors 120a and/or 120b are moved relative to the structures 402a-402f for capturing images of both surfaces 406a-406f and 408a-408f of each structure 402a-402f during evaluation of bubble formation potential in the structure 402a-402f A positioning mechanism 510a and 510b is associated with each detector 120a and 120b for movement of each detector 120a and 120b. Each positioning mechanism 510a and 510b is configured for moving the associated detector 120a or 120b in four-axes of motion for respectively positioning each detector 120a and 120b relative to the structures 402a-402f. For example the positioning mechanism 510a rotates the first detector 120a about an axis out of the page for capturing images of the first surfaces 406a-406f or front side of each structure 402a-402f The positioning mechanism 510a also moves the detector 120a in X, Y and Z axes directions relative to each structure 402a-402f.

Similarly, the positioning mechanism 510b moves the second detector 120b circumferentially about the structures 402a-402f to capture images of the second surface 408a-408f or back side of each structure 402a-402f during evaluation of bubble formation potential in the structure 402a-402f. The positioning mechanism 510b also moves the second detector 120b in X, Y and Z axes directions relative to each structure 402a-402b for capturing images of the second surface 408a-408f during evaluation of bubble formation potential in the structure 402a-402f. The first detector 120a and the second detector 120b may be moved one at a time or simultaneously. Usually, the first detector 120a and the second detector 120b are moved simultaneously so that images of the first surfaces 406a-406f and the second surfaces 408a-408f are captured at the same time. However, the detectors 120a and 120b may be moved at different speeds and frequencies. The detectors 120a and 120b may also be moved intermittently or continuously. The detectors 120a and 120b are still when capturing images or the detector settings are adjusted to capture clear images while the detector 120a or 120b is moving.

In another example, the sample holders 504 are moveable as well as the first detector 120a and second detector 120b as described herein for positioning the structure 402a-402f or the detectors 120a and 120b relative to one another for evaluating bubble formation potential of the structures 402a-402f as described herein. The sample holders 504 may be similar to the sample holders 404 described with reference to FIG. 4.

Figure 6:
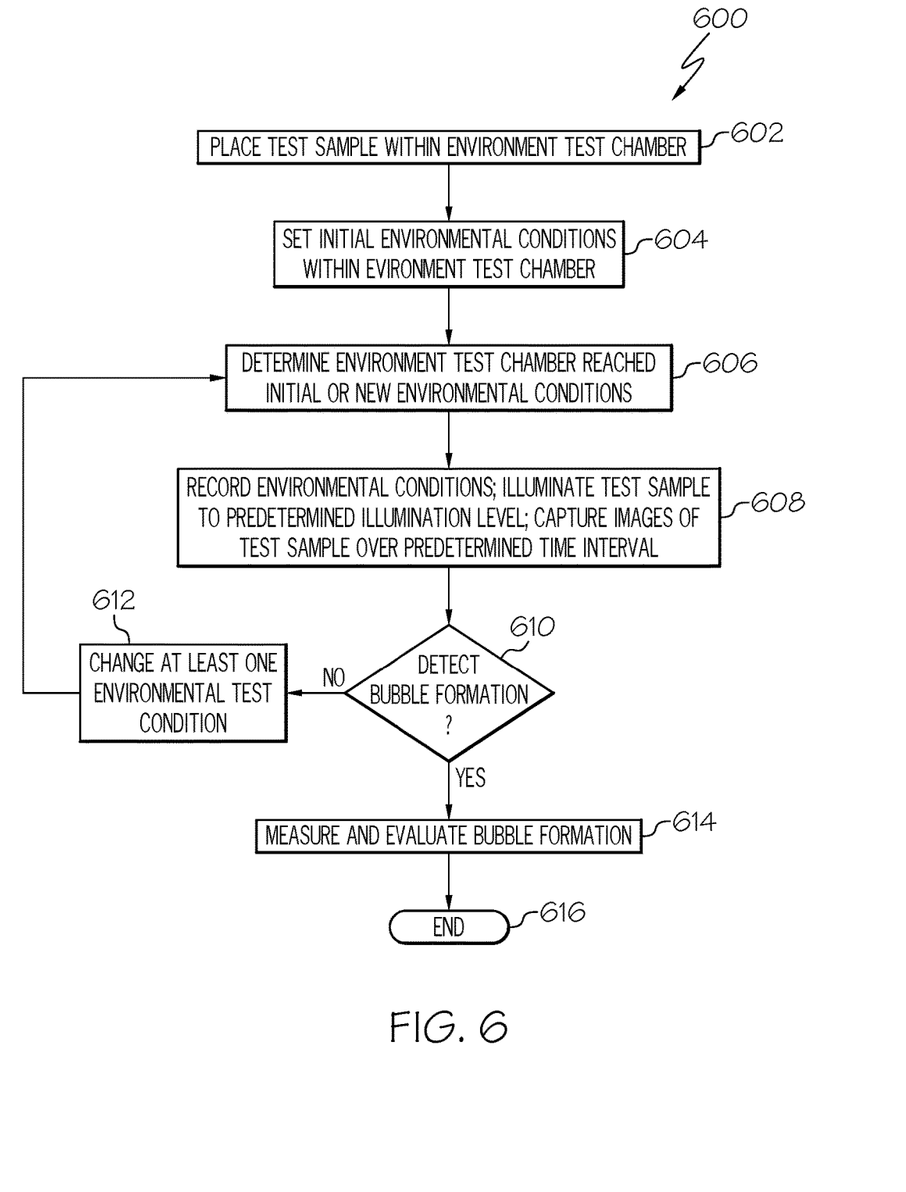
FIG. 6 is a flow chart of an example of a method for evaluation bubble formation potential in a structure in accordance with an example of the present disclosure.

FIG. 6 is a flow chart of an example of a method 600 for evaluation bubble formation potential in a structure or test sample in accordance with an example of the present disclosure. The method 600 may be embodied in and performed by either of the systems 100, 200 and 300 in FIGS. 1, 2 and 3, respectively. In block 602, a structure or test sample is placed within an environment test chamber. The structure may be held by a sample holder within the environment test chamber.

In block 604, a plurality of initial environmental conditions are set within the environment test chamber containing the structure. Examples of the plurality of environmental conditions that are set within the environment test chamber includes but is not necessarily limited to temperature, humidity, and pressure or vacuum. Other environmental conditions that may be set or detected may include type and level of radiation, type and concentration of particles, illumination level or brightness, and type and concentration of bacteria.

In block 606, a determination is made when the environment test chamber has reached the initial environmental conditions or new environmental conditions. In block 608, the environmental conditions are recorded in response to the environment test chamber reaching the initial environmental conditions. Images of the structure are captured over a predetermined time interval after the environment test chamber has reached the initial environmental conditions. In another example, images of the structure are also captured while the environment test chamber is reaching the initial environmental conditions or changing to at least one new environmental test condition.

The structure is preferably illuminated to a predetermined illumination level or brightness that enables a detector to capture images from which a bubble may be detected with a diameter or dimension as small as about $\frac{1}{32}$ inch or larger. Capturing images of the structure includes capturing images of the structure between an angle of about zero degrees and about 90 degrees relative to a plane of a surface of the structure.

In block 610, a determination is made if bubble formation is detected in the structure. If no bubble formation has been detected after expiration of the predetermined time interval, the method 600 advances to block 612. In block 612, at least one environmental condition is changed within the environment test chamber from a current plurality of environmental conditions, and the method 600 returns to block 606 where a determination is made whether the environment test chamber has reached the new environmental conditions. The method 600 then continues similar to that previously described to perform additional testing on the structure with the new environmental condition or conditions.

If bubble formation is detected in block 610, the method 600 advances to block 614. In block 614, the bubble formation is evaluated. In accordance with an example, a size and number of the bubbles are measured or determined for evaluating a bubble formation potential of the structure or test sample. The fewer and/or smaller the bubbles corresponds to a lower bubble formation potential under a certain set of environmental test conditions.

The method 600 ends at termination 616. The structure may be changed and the method 600 may begin again in block 602.

The flowchart and block diagrams in the Figures illustrate the architecture, functionality, and operation of possible implementations of systems, methods, and computer program products according to various examples of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular examples only and is not intended to be limiting of examples of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to examples of the disclosure in the form disclosed. Many modifications and variations will be apparent to those of ordinary skill in the art without departing from the scope and spirit of examples of the disclosure. The example was chosen and described in order to best explain the principles of examples of the disclosure and the practical application, and to enable others of ordinary skill in the art to understand examples of the disclosure for various examples with various modifications as are suited to the particular use contemplated.

Although specific examples have been illustrated and described herein, those of ordinary skill in the art appreciate that any arrangement which is calculated to achieve the same purpose may be substituted for the specific examples shown and that examples of the disclosure have other applications in other environments. This application is intended to cover any adaptations or variations of the present disclosure. The following claims are in no way intended to limit the scope of examples of the disclosure to the specific examples described herein.

What is claimed is:

1. A system for evaluating bubble formation potential in a structure, comprising:
   an environment test chamber;
   an environment controller for controlling a plurality of environmental conditions within the environment test chamber, wherein the plurality of environmental conditions comprise temperature, humidity and air pressure;

a detector for capturing images of a structure under test;
an illumination source for controlling illumination of the structure under test; and
a user interface coupled to the environment controller for adjusting the environmental conditions within the environment test chamber and the user interface is coupled to the illumination source for setting and adjusting illumination of the structure under test and the user interface is coupled to the detector for receiving the captured images and evaluating bubble formation potential in the structure under test based on the captured images.

2. The system of claim 1, wherein the illumination source and the detector are contained in the environment test chamber.

3. The system of claim 1, wherein at least the detector is outside the environment test chamber.

4. The system of claim 1, wherein the environment controller comprises:
a temperature controller for controlling the temperature within the environment test chamber;
a humidity controller for controlling the humidity within the environment test chamber; and
a pressure controller for controlling the air pressure within the environment test chamber.

5. The system of claim 1, wherein the environment test chamber comprises a portable environment test chamber.

6. The system of claim 1, wherein the user interface is at remote geographic location from the environment test chamber.

7. The system of claim 1, further comprising a sample holder for holding the structure under test, wherein the sample holder comprises a mechanism for positioning the structure under test at different angles relative to the detector.

8. The system of claim 1, wherein the user interface comprises a computer system, the system further comprising an algorithm running on the computer system, the algorithm being configured to evaluate the images from the detector to determine a bubble formation potential of the structure under test based on the environmental conditions within the environment test chamber.

9. The system of claim 1, further comprising at least one other environment controller for controlling at least one of a radiation level within the environment test chamber, a particle level within the environment test chamber and bacteria within the environment test chamber.

10. The system of claim 1 wherein the structure under test is a laminated structure comprising a decorative layer of material attached to a surface of another material.

11. The system of claim 1, wherein the illumination source is controllable to provide an illumination level of the structure under test that enables the detector to capture the images for detecting a bubble with a dimension or diameter of about 1/32 inch or larger.

12. The system of claim 1, further comprising:
a sample holder for holding a plurality of structures for evaluating bubble formation potential simultaneously; and
a plurality of detectors for capturing images of at least a front side and a back side of each structure.

13. The system of claim 12, wherein the sample holder is configured for moving the structures relative to the detectors.

14. The system of claim 12, further comprising a positioning mechanism associated with the detectors for moving the detectors relative to the structures.

15. A system for evaluating bubble formation potential in a structure, comprising:
an environment test chamber;
a temperature controller for controlling a temperature within the environment test chamber;
a humidity controller for controlling humidity within the environment test chamber;
a pressure controller for controlling an air pressure within the environment test chamber;
a detector for capturing images of a structure under test;
an illumination source for controlling illumination of the structure under test; and
a user interface coupled to the temperature controller, the humidity controller and the pressure controller for setting and adjusting environmental conditions within the environment test chamber, the user interface also being coupled to the illumination source for setting and adjusting illumination of the structure under test and the user interface also being coupled to the detector for receiving the captured images of the structure under test.

16. A method for evaluating bubble formation potential in a structure, comprising:
setting a plurality of initial environmental conditions within an environment test chamber containing the structure, wherein setting the plurality of initial environmental conditions comprises:
setting a temperature within the environment test chamber;
setting a humidity within the environment test chamber; and
setting a pressure or vacuum within the environment test chamber;
capturing images of the structure over a predetermined time interval;
detecting bubble formation in the structure; and
evaluating the bubble formation in response to detecting the bubble formation in the structure.

17. The method of claim 16, further comprising changing at least one environmental condition within the environment test chamber in response to one of not detecting bubble formation with a current plurality of environmental conditions or performing additional testing on the structure with the at least one environmental condition that is changed from the current plurality of environmental conditions.

18. The method of claim 16, wherein capturing images of the structure comprises illuminating the structure to provide an illumination level of the structure under test that enables a detector to capture the images for detecting a bubble with a dimension or diameter of about 1/32 inch or larger.

19. The method of claim 16, wherein capturing images of the structure comprises capturing images of the structure between an angle of about zero degrees and about 90 degrees relative to a plane of a surface of the structure.

20. The method of claim 16, wherein capturing images of the structure over a predetermined time interval comprises moving the structure relative to a detector that captures the images of the structure and/or moving the structure relative to the detector.

* * * * *